United States Patent [19]

Kiehs et al.

[11] Patent Number: 4,906,653
[45] Date of Patent: Mar. 6, 1990

[54] CONTROLLING MOLLUSCS WITH 2-(2-CHLORO-1-METHOXYETHOXY)-PHENYL METHYLCARBAMATE

[75] Inventors: Karl Kiehs, Lampertheim; Christoph Kuenast, Waldsee, both of Fed. Rep. of Germany

[73] Assignee: BASF Aktiengesellschaft, Ludwigshafen, Fed. Rep. of Germany

[21] Appl. No.: 154,226

[22] Filed: Feb. 10, 1988

[30] Foreign Application Priority Data

Feb. 27, 1987 [DE] Fed. Rep. of Germany ....... 3706358

[51] Int. Cl.$^4$ ...................... A01N 43/52; A01N 47/10
[52] U.S. Cl. .................................. 514/388; 514/479; 514/490
[58] Field of Search ................ 514/478, 479, 490, 388

[56] References Cited

U.S. PATENT DOCUMENTS 3,930,010  12/1975  Klopping ............................. 514/388

FOREIGN PATENT DOCUMENTS 1426233  2/1976  United Kingdom .

OTHER PUBLICATIONS

L. W. Getzin and S. G. Cole, Evaluation of Potential Molluscicides for Slug Control, Washington Agricultural Experiment Stations, vol. 658 (1964).
P. J. Hunter and D. L. Johnston, J. of Economic Entomology, vol. 63, pp. 305–306 (1970).

Primary Examiner—Allen J. Robinson
Attorney, Agent, or Firm—Keil & Weinkauf

[57] ABSTRACT

A method for controlling molluscs with 2-(2-chloro-1-methoxyethoxy)phenyl methylcarbamate of the formula

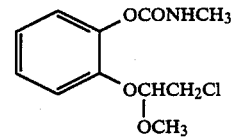

and molluscicides containing a mixture of 2-(2-chloro-1-methoxyethoxy)phenyl methylcarbamate with methyl benzimidazol-2-ylcarbamate is described.

5 Claims, No Drawings

CONTROLLING MOLLUSCS WITH 2-(2-CHLORO-1-METHOXYETHOXY)-PHENYL METHYLCARBAMATE

The present invention relates to a method for controlling molluscs, in particular terrestrial and amphibious snails and slugs, with 2-(2-chloro-1-methoxyethoxy)-phenyl methylcarbamate.

It is known that various organic compounds, for example methaldehyde and 4-methylthio-3,5-diemthyl-phenyl N-methylcarbamate, can be used for controlling snails and slugs, and various other N-methylcarbamates may have an immobilizing effect or in some cases even a slight destructive action on snails and slugs [L.W. Getzin and S.G. Cole, Evaluation of potential molluscicides for slug control, Washington Agr. Exp. Sta. Bull. Vol. 658 (1964); P.J. Hunter and D.L. Johnston, J. Econ. Entomol. 63 (1970), 305-306]. However, this action is too weak for use in, for example, agriculture. This also applies to commercial products which have been introduced, for example those which contain 2-(1-methylethoxy)phenyl N-methylcarbamate (Getzin, Cole, Table 3, page 6).

Snails and slugs are significant pests in temperate, subtropical and tropical crops. New cultivation techniques, in particular no tillage and minimum tillage, lead to increased damage by snails and slugs. Since, because of their ecology, many species of snails and slugs are ubiquitous, such species have spread into regions in which they were not originally present (for example Achatina fulica from East Africa to Australia and North America).

We have found that 2-(2-chloro-1-methoxyethoxy)-phenyl methylcarbamate (cloethocarb), which is disclosed as an insecticidal active ingredient in DE-C-22 31 249, surprisingly has pronounced molluscicidal properties; it is very useful for controlling snails and slugs in agriculture and horticulture.

We have furthermore found that the fungicidal active ingredient methyl benzimidazol-2-ylcarbamate (carbendazim) in combination with cloethocarb has a synergistic effect in controlling molluscs. This effect occurs if the weight ratio of cloethocarb to carbendazim is from 0.01:1 to 50:1, preferably from 1:1 to 30:1, in particular from 10:1 to 20:1.

The molluscicidal action of cloethocarb and combinations of cloethocarb and carbendazim extends to terrestrial and amphibious snails and slugs, for example those of the genera Deroceras (Agriolimax), Limax, Helix, Helicogona, Cepaea, Milax, Lymnaea (Galba), Achatina, Theba, Cochlicella, Helicarion and Vaginulus. The snail and slug pests include, for example, the slugs Arion ater, A. lusitanicus, A. hortensis, Agriolimax reticulatus, Limax flavus, L. maximus, Milax gagates, Mariaella dursumierei, Helicarion salius, Vaginula hedleyi and Pamarion pupillaris and the snails Helix aspersa spp., Cepaea nemoralis, Theba pisana, Achatina fulica, A. zanzibarica, Limicolaria kambeul, Bradybaena spp., Cochlodina spp., Helicella spp. and Euomphalia spp.

Suitable formulations for molluscicides are described in, for example, DE-A-3,503,608 and DE-A-3,500,468; they require in general a carrier, an edible substance or a bait, a binder and the active ingredient.

Examples of suitable (solid) carriers are powdered natural minerals, such as kaolins, clays, talc, chalk, quartz, attapulgite, montmorrilonite or diatomaceous earth, and powdered synthetic minerals, such as finely divided silica, alumina and silicates; examples of suitable solid carriers for pellets are crushed and fractionated natural minerals, such as calcite, marble, pumice, sepiolite, dolomite, synthetic pellets of inorganic and organic meals and pellets of organic material, such as sawdust, coconut shells, corn cobs and tobacco stalks.

Mixing with baits such as cereal products (eg. wheat, oats, barley, rye, corn or rice in the form of grains, flour, coarse meal, bran, germs or bread), oil cake (for example from cottonseed, peanuts, sunflower or poppy seed), malt, yeasts, sugar beet molasses or residues from fruit pressing, or with species-specific or snail- and slug-specific baits is particularly advantageous, suitable binders, adhesives, stabilizers and microbial inhibitors being used in each case; it is advantageous to add substances which repel birds and mammals, and organic or inorganic dyes or pigments. The purpose of such additives is to repel non-target organisms and to ensure that the action lasts for as long a period as possible.

Another preferred form of application is seed dressing with a formulation conventionally used for dressings.

The content of active ingredient in the individual application forms can vary within wide limits, for example from 0.001 to 90, preferably from 1 to 10, % by weight in the case of grain formulations and from 10 to 90% by weight in the case of seed dressings.

The application rate of active ingredient is from 0.3 to 30, preferably from 1 to 10, kg/ha.

FORMULATION EXAMPLE 1

2 kg of cleothocarb, 8 kg of calcium stearate, 0.2 kg of sodium benzoate, 20 kg of chalk, 0.5 kg of a blue dye and 69.3 kg of wheat bran are mixed in a mixer. This mixture is then moistened with sufficient water and kneaded in a kneader. Thereafter, the moist mixture is shaped in an extruder to give snail or slug bait pellets having a diameter of 3 mm, and dried at no higher than 60° C.

FORMULATION EXAMPLE 2

To prepare a seed dressing,
480 g of cloethocarb,
20 g of a commercial phenolsulfonic acid/urea/formaldehyde condensate,
40 g of an ethylene/propylene block copolymer having a molecular weight of 10,000,
2 g of xanthane rubber,
0.5 g of Rhodamine FB,
80 g of 1,2-propylene glycol and
5 g of silicone antifoam
are mixed and the mixture is made up to 1 liter with water.

USE EXAMPLE 1

Shallow plastic trays (40 x 55 cm) are filled with moist, steam-treated soil, on which 100 g of lettuce leaves are placed. In test series, 18 slugs (sexually mature individuals of Arion lusitanicus) are used per container, 0.15 g of slug pellets is distributed uniformly over the soil, and the trays are closed with plastic nets. Dead and damaged animals are counted at intervals of 1 or 3 days; the mean result is shown in the Table below, the numbers indicating the relevant percentages of individuals affected in the test series. Dead slugs are those which do not react when touched, and damaged slugs are those which have externally detectable damage but still react when touched.

TABLE 1

| | Number of days | | | | | | | |
|---|---|---|---|---|---|---|---|---|
| | 1 | | 2 | | 3 | | 4 | |
| | Condition | | | | | | | |
| | Dead | Damaged | Dead | Damaged | Dead | Damaged | Dead | Damaged |
| Methaldehyde slug pellets | 0 | 10 | 0 | 5–10 | 0 | 10–20 | 0 | 10–20 |
| Cloethocarb slug pellets | 0 | 70–80 | 10–20 | 50–60 | 50 | 20–30 | 80–90 | 10–20 |
| Control | 0 | 0 | 0 | 0 | 0 | 0 | 0 | 0 |

USE EXAMPLE 2

The action of the fungicidal active ingredient carbendazim in combination with cloethocarb was investigated. When a formulation containing 4% by weight of cloethocarb and 0.2% by weight of carbendazim was used, a remarkable increase over the action of cloethocarb was observed. The procedure and evaluation correspond to Use Example 1. The results are summarized in Table 2.

TABLE 2

| | No. of days | | | | | | | | | |
|---|---|---|---|---|---|---|---|---|---|---|
| | 1 | | 2 | | 3 | | 6 | | 7 | |
| | Condition | | | | | | | | | |
| | Dead | Damaged | Dead | Damaged | Dead | Damaged | Dead | Damaged | Dead | Damaged |
| 4% by weight of cloethocarb | 5.6 | 38.9 | 38.9 | 5.6 | 61.1 | — | 83.3 | — | 83.3 | — |
| 4% by weight of cloethocarb + 0.2% by weight of carbendazim | — | 44.4 | 88.9 | 11.1 | 94.4 | 5.6 | 100 | — | 100 | — |

USE EXAMPLE 3

Comparison of 3,5-dimethyl-4-methylmercaptophenyl N-methylcarbamate (commercial antislug product; common name mercaptodimethur) and cloethocarb (contact test; immediate action)

Experimental procedure:

Slug pellets obtained as stated in Example 1 were finely milled in a mortar, and the appropriate amount (based on content of active ingredient) is distributed in a Petri dish (diameter 10 cm). 5 slugs (Arion ater) were used, and the percentage damage was determined after 5 h.

| g of active ingredient/ Petri dish | 0.01 | 0.006 | 0.004 | 0.001 | 0.0006 | Control |
|---|---|---|---|---|---|---|
| Mercaptodimethur | 100 | 0 | 0 | 0 | 0 | 0 |
| Cloethocarb | 100 | 100 | 80–100 | 20–40 | 0 | 0 |

We claim:

1. A method for controlling molluscs, wherein the plants to be protected from molluscs, and/or the environment of the said plants, are treated with a molluscicidally effective amount of a composition containing a carrier, a bait and, as a molluscicidal agent an effective amount of 2-(2-chloro-1-methoxyethoxy)phenyl methylcarbamate of the formula

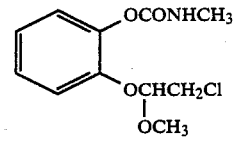

2. The method of claim 1, wherein the molluscs are terrestrial or amphibious snails or slugs.

3. The method for controlling molluscs as defined in claim 1, wherein 2-(2-chloro-1-methoxyethoxy)phenyl methylcarbamate is used in combination with methyl benzimidazol-2-ylcarbamate in a weight ratio of from 0.01:1 to 50:1.

4. A molluscicide composition which comprises: a carrier, a bait, and a molluscicidally effective amount of a combination of 2-(2-chloro-1-methoxyethoxy)phenyl methylcarbamate and methyl benzimidazol-2-ylcarbamate in a weight ratio of from 0.01:1 to 50:1.

5. A molluscicide composition which comprises: a carrier, a bait, and a molluscicidally effective amount of 2-(2-chloro-1-methoxyethoxy)-phenyl methylcarbamate.

* * * * *